(12) United States Patent
Kataoka

(10) Patent No.: US 6,526,814 B1
(45) Date of Patent: Mar. 4, 2003

(54) HOLDER FOR THROW-AWAY TIP WITH SENSOR

(75) Inventor: Hideaki Kataoka, Kyoto (JP)

(73) Assignee: Kyocera Corporation, Kyoto (JP)

( * ) Notice: Subject to any disclaimer, the term of this patent is extended or adjusted under 35 U.S.C. 154(b) by 199 days.

(21) Appl. No.: 09/613,966

(22) Filed: Jul. 11, 2000

(30) Foreign Application Priority Data

Sep. 29, 1999 (JP) ............................................ 11-277548
Dec. 3, 1999 (JP) ............................................ 11-345248
Dec. 16, 1999 (JP) ............................................ 11-357942

(51) Int. Cl.$^7$ ................................................ G01N 3/58
(52) U.S. Cl. ........................................ 73/104; 73/866.5
(58) Field of Search ............................... 73/866.5, 104, 73/493

(56) References Cited

U.S. PATENT DOCUMENTS 4,869,119 A * 9/1989 Bachand et al. ............ 73/866.5
4,885,530 A * 12/1989 Mayer et al. .................. 73/104
5,000,036 A * 3/1991 Yellowley et al. ............. 73/104

FOREIGN PATENT DOCUMENTS

| JP | 3-503862 | 8/1991 |
| JP | 3-120323 | 12/1991 |
| JP | 09-038846 | 2/1997 |

* cited by examiner

Primary Examiner—Robert Raevis
(74) Attorney, Agent, or Firm—Hogan & Hartson, LLP

(57) ABSTRACT

There has been a demand for a holder for properly holding a throw-away tip with an abrasion sensor. The holder (1) has a tip mounting portion (4) provided in an end portion thereof and formed with a pocket (5). A pair of probe insertion holes (19) are formed in a bottom face (6) of the pocket (5). The probe insertion holes (19) are provided adjacent a front face (40A) of the tip mounting portion (4). Probes (41) are fixed in a probe fixture (44) which is fitted in the probe insertion holes (19). The holder makes the probes (41) less liable to suffer from stresses during a cutting process, and ensures proper electrical connection between the probes (41) and the abrasion sensor of the throw-away tip (2). (FIG. 1).

9 Claims, 14 Drawing Sheets

HOLDER FOR THROW-AWAY TIP WITH SENSOR

This application claims priority benefits under 35 USC section 119 on the basis of Japanese Patent Applications No. 11-277548, No. 11-345248 and No. 11-357942, the disclosure thereof being incorporated herein by reference.

BACKGROUND OF THE INVENTION

1. Field of the Invention

The present invention relates to a holder for holding a throw-away tip with an abrasion sensor. More specifically, the invention relates to a holder having probes electrically connectable to an abrasion sensor of a throw-away tip.

2. Description of Related Art

Automatic detection of expiration of the life of a cutting tool has been proposed which is achieved by detecting the abrasion degree of a cutting ridge of the cutting tool.

For example, Japanese Unexamined Utility Model Publication No. 3-120323 (1991) discloses a throw-away tip having a sensor line of a conductive film provided along a cutting ridge on a flank thereof. It is also disclosed that the sensor line has a width conforming to an allowable abrasion width. In accordance with the throw-away tip disclosed in this publication, the sensor line is worn as the cutting ridge is worn, so that the expiration of the life of the cutting ridge can be detected when the sensor line is cut off.

Further, Japanese Unexamined Patent Publication No. 9-38846 (1997) proposes an ordinary cutting tool (not a throw-away tip) which has a thin film circuit on a flank thereof, wherein the expiration of the life of the cutting tool is automatically detected by sensing a change in electrical resistance which occurs due to abrasion of the thin film circuit as the flank is worn.

For the detection of the abrasion of the cutting ridge, the aforesaid method is preferred in which the sensor line is provided along the cutting ridge on the flank of the cutting tool to sense the change in the electrical resistance of the sensor line.

Where this method is applied to the throw-away tip, however, it is difficult in practice to connect the sensor line provided along the cutting ridge to an external detection circuit and the like.

More specifically, the throw-away tip is a disposable tip, and is very small with a size of less than 1 cm$^3$. During the cutting process, the tip in operation is subjected to a cutting fluid (water or oil) and slugs. However, no technique has been established for connecting the sensor line formed on the small throw-away tip to the external detection circuit and the like without any trouble in such a machining environment.

Lead wires for extracting a signal from a sensor line of the throw-away tip may be provided in a holder for the throw-away tip. However, consideration should be given to the holder for preventing the lead wires from contacting the slugs during the cutting process and for preventing the lead wires from being cut off. A holder given such consideration has not been put into practical use.

SUMMARY OF THE INVENTION

To solve the aforesaid problems, it is an object of the present invention to provide a holder for properly holding a throw-away tip with an abrasion sensor.

The holder according to the present invention has a shank and a tip mounting portion provided at an end of the shank. The tip mounting portion has a pocket for fixedly holding a throw-away tip with a sensor. The pocket opens into an upper face of the tip mounting portion, a front face of the tip mounting portion which is to be flush with a front flank of the throw-away tip, and a side face of the tip mounting portion which is to be flush with a side flank of the throw-away tip. The pocket has a bottom face which serves as a seat face for receiving an under face of the throw-away tip placed thereon, and has a rear face and a side face (inward side face) which serve as restriction surfaces to be brought into abutment against side faces of the throw-away tip. The tip mounting portion is formed with a probe insertion hole which opens toward the pocket. Probes each having a distal end electrically connectable to the sensor of the throw-away tip are fitted in the probe insertion hole in an electrically insulative manner with respect to the tip mounting portion.

With this arrangement, the abrasion degree of the sensor of the throw-away tip can assuredly be detected in an electrical manner with the use of the probes. The probes are fitted in the probe insertion hole, so that contacts between the probes and the throw-away tip are not exposed to the outside. Therefore, slug ejection is hindered neither by the probes nor by the electrical contacts between the probes and the sensor during the cutting process.

Lead wires connected to proximal ends of the probes are preferably accommodated within a channel formed in the holder. With this arrangement, the slug ejection is not hindered by the lead wires.

A seat may be provided between the seat face and the tip when the throw-away tip is mounted in the pocket. With this arrangement, a holder body can be protected from a shock which may occur when the throw-away tip is heavily damaged or chipped.

The probes are preferably fixed in the probe insertion hole by an electrically insulative probe fixture. The use of the probe fixture ensures easier fixing of the probes.

The distal ends of the probes may be coated with a conductive rubber. Thus, the electrical connection between the probes and the throw-away tip can be improved.

The tip mounting portion may be provided with a removable cover. With the provision of the cover, an operation can easily be performed to connect the probes and the lead wires.

The probe insertion hole of the tip mounting portion may open into the seat face of the pocket. In this case, the probe insertion hole is preferably provided adjacent the front face of the tip mounting portion. The probe insertion hole provided adjacent the front face of the tip mounting portion is less liable to suffer from a stress. Therefore, there is a reduced possibility that the probes are broken even if the throw-away tip is broken into pieces.

The probe insertion hole may open into at least one of the restriction surfaces of the pocket. With the probe insertion hole opening into the restriction surface, there is a reduced possibility that the probes are broken even if the throw-away tip is damaged or broken during the cutting process. This is because a stress is not concentrated on the restriction surfaces during the cutting process.

As described above, the restriction surfaces include two faces, i.e., the rear face and the inward side face. The probe insertion hole may include two probe insertion holes which are provided one in each of the restriction surfaces or both in one of the restriction surfaces.

Embodiments of the present invention will hereinafter be described in detail with reference to the attached drawings.

DESCRIPTION OF THE PREFERRED EMBODIMENTS

Figure 1:
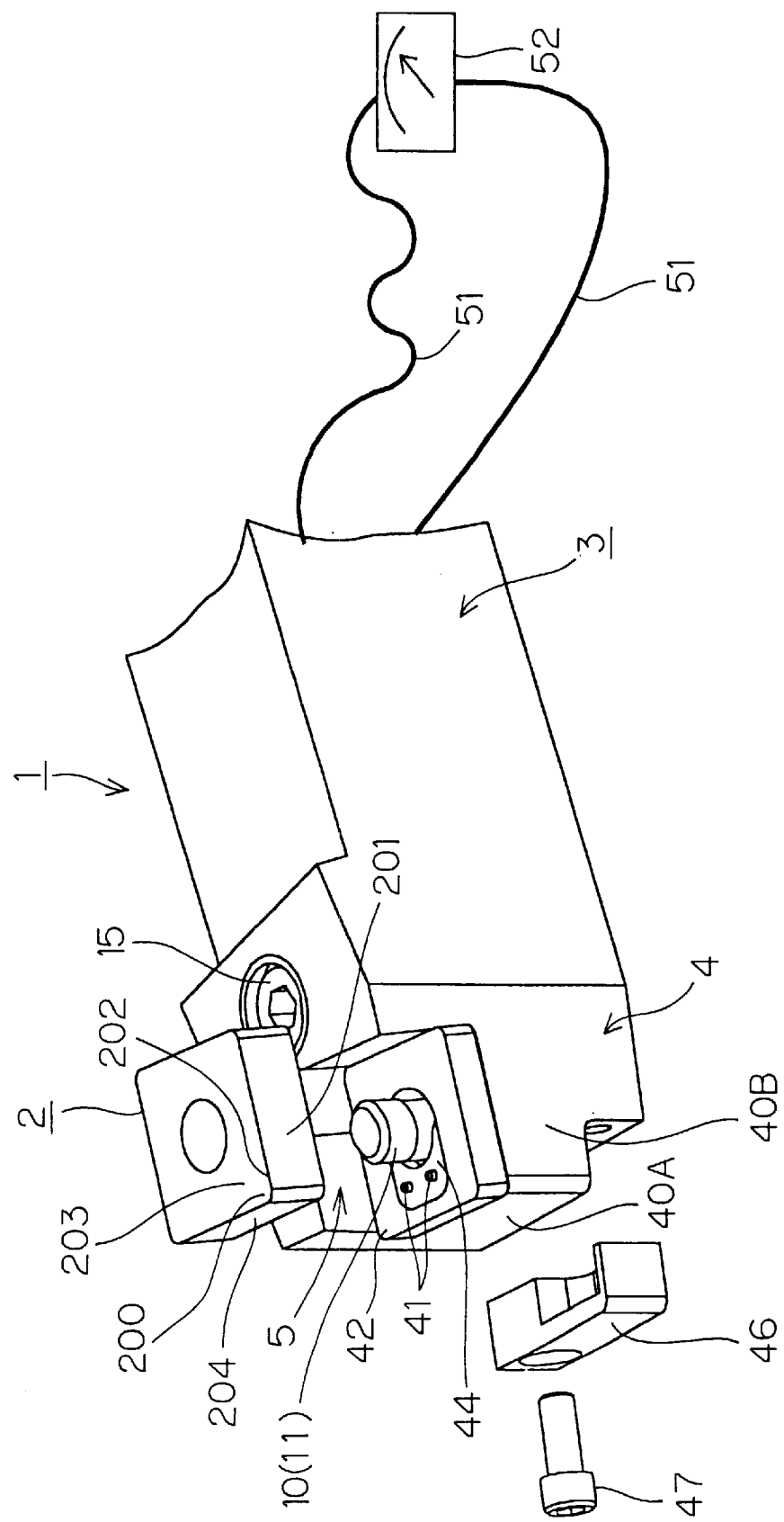
FIG. 1 is a diagram illustrating a holder for a throw-away tip in accordance with one embodiment of the present invention.
Figure 2:
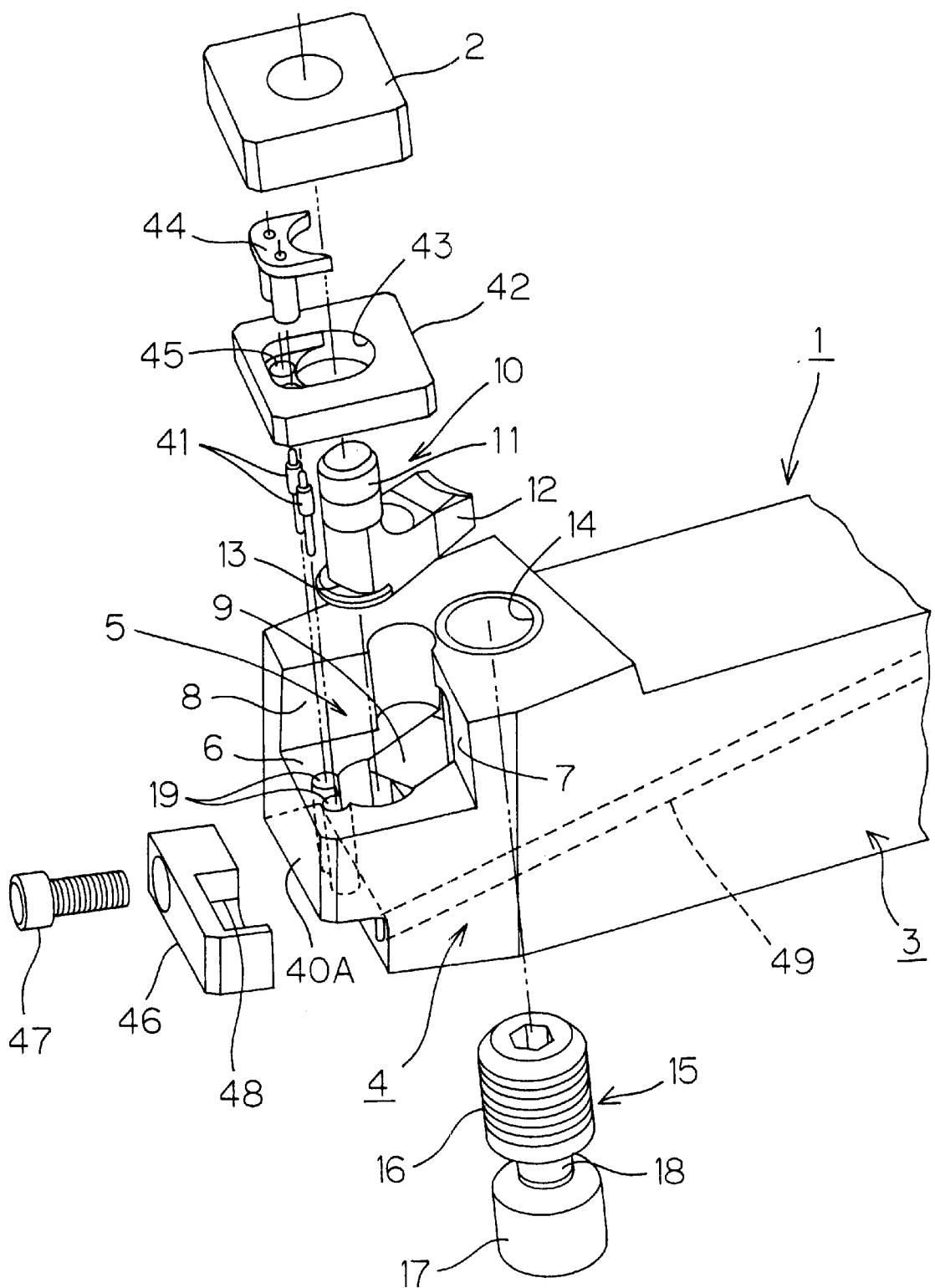
FIG. 2 is an exploded perspective view of the holder shown in FIG. 1.

FIG. 1 illustrates a holder 1 for a throw-away tip in accordance with one embodiment of the present invention. FIG. 2 is an exploded perspective view of the holder 1 shown in FIG. 1. Referring to FIGS. 1 and 2, the holder 1 is adapted to hold a throw-away tip 2. The holder 1 includes a shank 3 to be attached to a tool post not shown, and a tip mounting portion 4 provided at a distal end of the shank 3 integrally formed with the shank 3. Although the shank 3 longitudinally extends to the right in FIGS. 1 and 2, a rear portion thereof is not shown for convenience of explanation.

The holder 1 is composed of an alloy steel. Examples of the alloy steel include chromium-molybdenum steel, nickel-chromium steel, nickel-chromium-molybdenum steel, and alloy steels comprising a carbon alloy steel base consisting of iron and five elements including C, Si, Mn, P and S and at least one element selected from chromium, tungsten, manganese, molybdenum, vanadium and the like.

The tip mounting portion 4 has a pocket 5. The pocket 5 is a recess which opens into an upper face, a front face and one side face (a forward side face in FIGS. 1 and 2) of the tip mounting portion 4. A bottom face 6 of the pocket 5 serves as a seat face for receiving the throw-away tip 2 placed thereon with intervention of a seat 42. A rear face 7 and a side face (an inward side face in FIGS. 1 and 2) 8 of the pocket 5 serve as restriction surfaces which are brought into abutment against side faces of the throw-away tip 2.

The pocket 5 has a lever groove 9 formed in the bottom face 6 thereof. The groove 9 receives a lever 10 having an L shape in elevation. The lever 10 has a hollow cylindrical action portion 11 extending upward, a power applying portion 12 laterally extending from a lower portion of the action portion 11, and a support portion 13 defining a juncture between the action portion 11 and the power applying portion 12.

The tip mounting portion 4 has a clamp hole 14 provided adjacent the pocket 5, more specifically adjacent an intersection between the rear face 7 and the side face 8. The clamp hole 14 is a through-hole extending through the tip mounting portion 4 from the upper surface to the lower surface thereof, and an upper portion of an interior surface of the clamp hole 14 is threaded. The clamp hole 14 has a midportion which communicates with the lever groove 9. A clamp bolt 15 is screwed into the clamp hole 14 from the lower side. The clamp bolt 15 has a thread portion 16 having a threaded circumference, a shank portion 17 not threaded, and a smaller diameter shank portion 18 vertically extending between the thread portion 16 and the shank portion 17.

When the lever 10 is accommodated in the lever groove 9 with the clamp bolt 15 screwed into the clamp hole 14, the power applying portion 12 is fitted in a space defined by the smaller diameter shank portion 18 within the clamp hole 14. Then, the clamp bolt 15 is vertically moved in threading engagement with the clamp hole, whereby the power applying portion 12 of the lever 10 engaged with the smaller diameter shank portion 18 is vertically moved. Thus, the lever 10 is pivoted about the support portion 13 so that the action portion 11 of the lever 10 is shifted between a state where the throw-away tip 2 is fixedly held between the rear restriction surface 7 and the inward restriction surface 8 and a state where the throw-away tip 2 is replaceable. Therefore, the throw-away tip 2 can be restricted by the rear restriction surface 7 and the inward restriction surface 8 by adjusting the insertion depth of the clamp bolt 15, for example, by means of a hexagonal wrench after the tip 2 is set around the action portion 11 of the lever 10.

The tip mounting portion 4 has a pair of probe insertion holes 19 which open into the bottom face 6 thereof. The probe insertion holes 19 are provided adjacent the front face 40A of the tip mounting portion 4. A pair of probes 41 are fitted in the probe insertion holes 19.

The seat 42 is provided in the pocket 5. The seat 42 serves as a protective member for preventing the holder 1 from being influenced by the throw-away tip 2 when the tip 2 is heavily damaged or chipped. The seat 42 is composed of a cemented carbide. The seat 42 has substantially the same plan configuration as the throw-away tip 2, i.e., a generally square plan shape. The seat 42 has a hole 43 formed in the center thereof through which the action portion 11 of the lever 10 projects. The seat 42 is further formed with an engagement recess 45 in which a probe fixture 44 is fitted.

The probe fixture 44 is composed, for example, of a heat-resistant and electrically insulative resin. When the probe fixture is brought into engagement with the engagement recess 45, lower portions of the probe fixture project downward from the seat 42. The probes 41 are inserted into the probe fixture 44 from the lower side and fixed therein. The seat 42 engaged with the probe fixture 44 in which the probes 41 are fixed can be retained in a proper position of the tip mounting portion 4 of the holder 1 by bringing the probe fixture 44 projecting downward from the seat 42 into engagement with the probe insertion holes 19 formed in the bottom face 6.

The tip mounting portion 4 is provided with a removable cover 46 which defines a lower portion of the front face 40A. The cover 46 is fixed to the tip mounting portion 4, for example, by a bolt 47. The cover 46 has a recess 48 formed in an inward portion thereof. The recess 48 serves as a space for accommodating the lower portions of the probe fixture 44 and lower portions of the probes 41. With the cover 46 removed from the tip mounting portion 4, the lower portions of the probes 41 project downward from the probe insertion holes 19. On the other hand, a lead wire channel or hole 49 is formed adjacent an under surface of the holder 1, and lead wires are routed through the channel or hole 49. With the cover 46 removed, an operation can easily be performed to electrically connect the lead wires drawn out of distal ends of the channel or hole 49 to the lower portions of the probes 41.

Junctions between the probes 41 and the lead wires can completely be concealed by fixing the cover 46 to the tip mounting portion 4 with the bolt 47, so that the cutting operation can be performed without any trouble.

Figure 3:
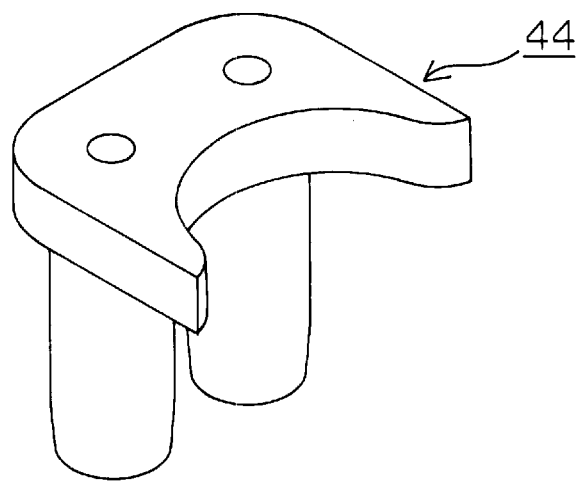
FIG. 3 is an enlarged perspective view of a probe fixture.
Figure 4:
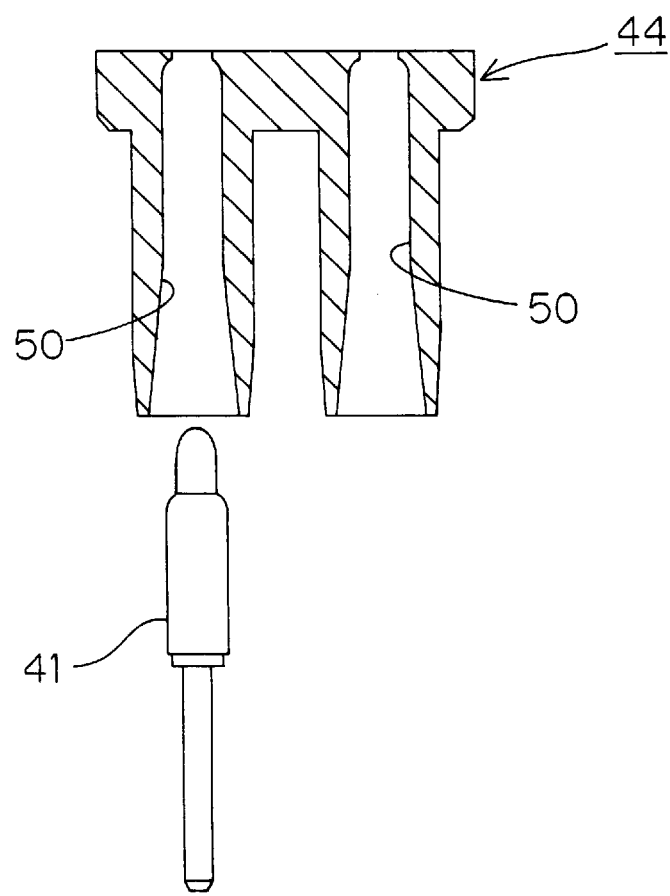
FIG. 4 is a diagram illustrating the probe fixture in vertical section and an exemplary probe to be engaged with the probe fixture.

FIG. 3 is an enlarged perspective view of the probe fixture 44, and FIG. 4 illustrates the probe fixture 44 in vertical section and the probe 41 to be engaged with the probe fixture 44.

As shown in FIGS. 3 and 4, the probe fixture 44 has a pair of probe insertion holes 50 for holding the pair of probes 41 in a predetermined spaced relation. Lower portions of the probe insertion holes 50 are flared for easy insertion of the probes 41. The probe insertion holes 50 each have an inner diameter which is equal to the maximum outer diameter of the probes 41. The probes 41 are softly squeezed into the probe insertion holes 50 and fixed therein.

With the probes 41 fitted in the probe fixture 44, the probes 41 are electrically isolated from the seat 42 and the tip mounting portion 4.

Referring again to FIG. 1, distal ends of the probes 41 slightly project upward from the seat 42. The distal ends of the probes 41 are resiliently biased upward by springs or the like incorporated in the probes 41. When the throw-away tip 2 is placed on the seat 42, the distal ends of the probes 41 are brought into resilient contact with sensor contact portions provided on an under face of the throw-away tip 2. Thus, a resistance signal of the abrasion sensor of the throw-away tip 2 can be extracted and applied to an external resistance meter 52 via the probes 41 and the lead wires 51 connected to the probes 41.

In the embodiment described above, the cutting process is achieved by bringing a workpiece (metal work to be cut) into contact with the throw-away tip 2 from the side of the side face 40B of the holder 1 and advancing the holder 1 to the side of the front face 40A while turning the workpiece. At this time, a nose portion 200 located in a forward left corner of the throw-away tip 2 as seen in FIG. 1 and a cutting edge 202 located along an upper edge of a side flank 201 are mainly used for the cutting process. Therefore, stresses are generated in the cutting edge 202 directly serving for the cutting and in a portion of a rake face 203 of the throw-away tip 2 adjacent to the cutting edge 202 suffering from an attack by slugs during the cutting process, so that heat is generated to a high temperature. Similarly, a stress is concentrated on a part of the tip mounting portion 4 of the holder 1 adjacent to the side face 40B located below the rake face 203 of the throw-away tip 2. By the stresses generated in the throw-away tip 2, the cutting edge 202 and the rake face 203 are abraded and sometimes chipped. The chipping may cause breakage of the throw-way tip 2. If the probe insertion holes 19 were provided in a portion of the bottom face 6 adjacent to the side face 40B on which a stress is concentrated as in the throw-away tip 2, the breakage of the throw-away tip 2 would influence the probes 41 which contact the under face of the throw-away tip 2.

In this embodiment, on the contrary, the probe insertion holes 19 are provided adjacent the front face 40A of the tip mounting portion 4 which is flush with a front flank 204 of the throw-away tip 2.

The probe insertion holes 19 thus provided adjacent the front face 40A of the tip mounting portion 4 are less liable to suffer from the stresses. There is a reduced possibility that the probes 41 within the probe insertion holes 19 are broken even if the throw-away tip 2 is broken into pieces.

More generally speaking, the holder for fixedly holding the throw-away tip in accordance with this embodiment is characterized in that, with the throw-away tip attached to the holder, the probe insertion holes are provided in positions apart from a face of the holder flush with the flank of the throw-away tip being used for the cutting. In other words, one of the features of the invention is that the probe insertion holes are provided in positions of the holder which are less liable to suffer from the stresses generated during the cutting process.

Figure 5A:
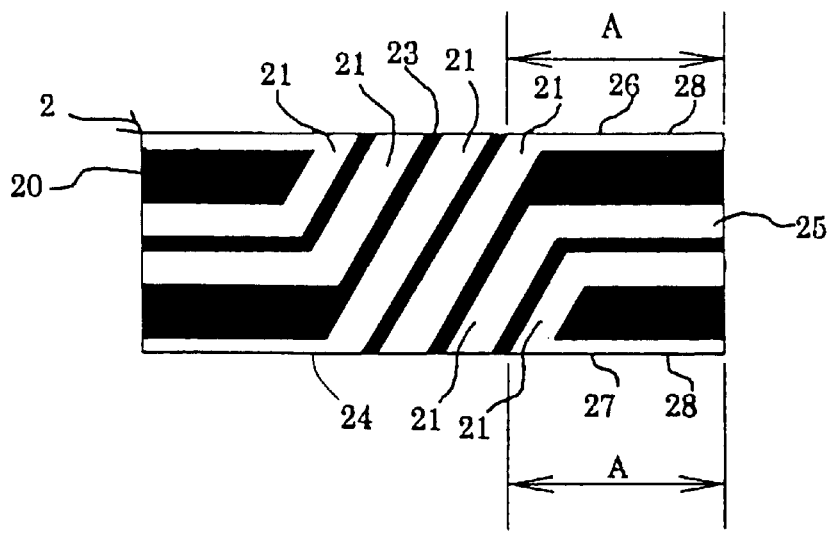
FIGS. 5A and 5B are a side view and a plan view, respectively, of the throw-away tip to be held by the holder according to the embodiment of the invention.
Figure 5B:
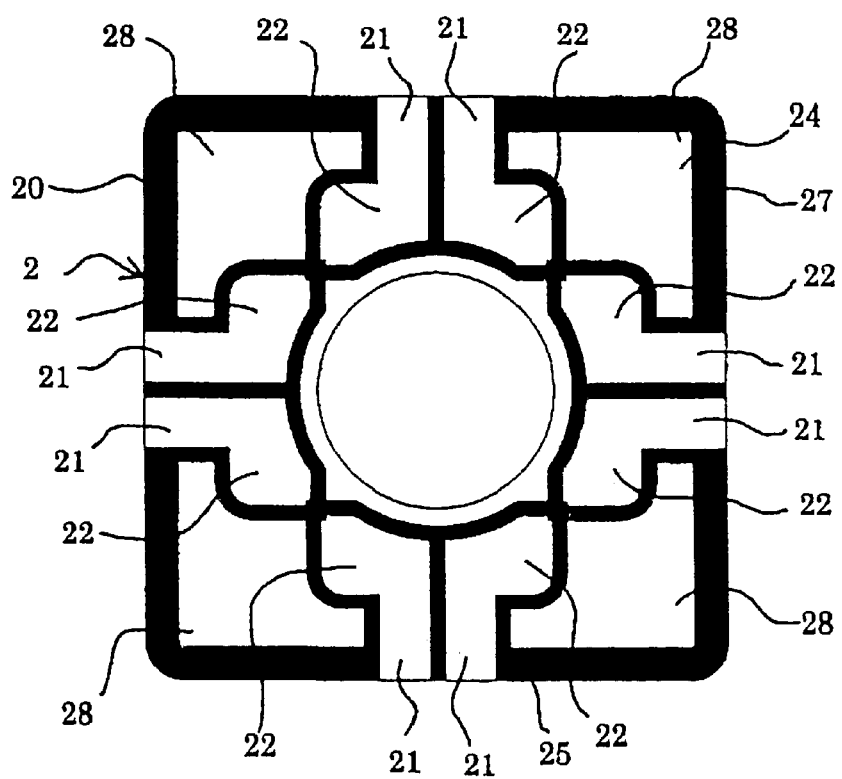
Figure 6:
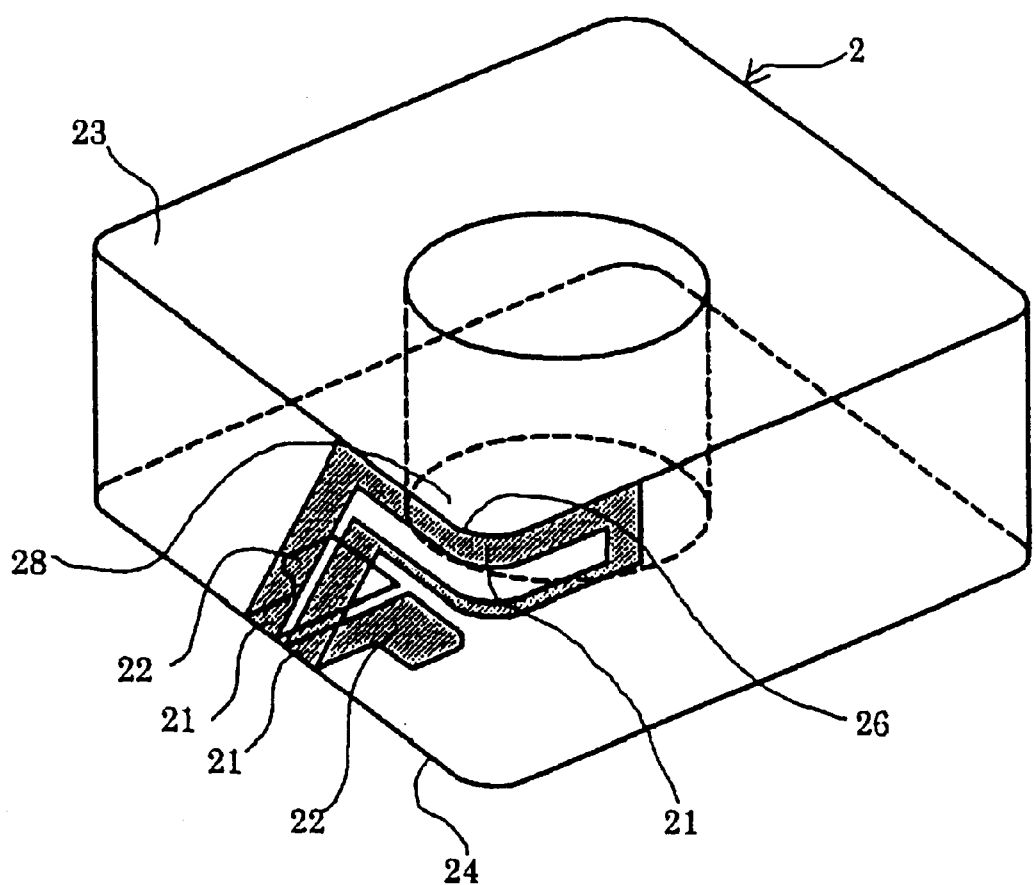
FIG. 6 is a schematic perspective view of the throw-away tip for explaining a pattern of an abrasion sensor of the throw-away tip.

FIGS. 5A, 5B and 6 illustrate an example of the throw-away tip 2 to be held by the holder according to this embodiment. As shown, the throw-away tip 2 includes a base 20 of a silicon nitride based ceramic, and abrasion sensors 21 each comprised of a conductive film circuit formed on the base 22 and having opposite ends 22. The throw-away tip 2 has an upper face 23, a lower face 24, flanks 25 and cutting ridges 26, 27.

The throw-away tip 2 is of a so-called negative type in which the cutting ridges 26, 27 on the upper and lower faces (23, 24) thereof are usable for cutting. The throw-away tip has no distinction between the upper and lower sides thereof. Eight nose portions 28 on eight corners of the throw-away tip can be used for the cutting. For convenience of explanation, one of the opposite faces of the base 2 is herein called "upper face 23" and the other surface is called "lower face 24".

FIG. 6 is an explanatory diagram illustrating the pattern of one of the abrasion sensors 21 in an easily understandable manner. The pattern is three-dimensionally illustrated as seen through the throw-away tip 2. As shown, the abrasion sensor 21 having the opposite ends 22 on the lower face 24, for example, extends onto the flank 25 from the ends 22, then traverses the flank 25 to reach the cutting ridge 26 defined by a boundary between the upper face 23 and the flank 25, and extends along the cutting ridge 26.

Actually, the throw-away tip 2 has four abrasion sensors 21 each having opposite ends 22, 22 on the lower face 24, and respectively extend to reach the cutting ridges 26 of the four nose portions 28 on the upper face 23. The upper face 23 has the same configuration as the lower face 24. The throw-away tip further has four abrasion sensors 21 each having opposite ends 22, 22 on the upper face 23, and respectively extend to reach the cutting ridges 27 of four nose portions 28 on the lower face 24.

When the throw-away tip 2 of such a construction is attached to the holder 1, the ends 22 of one of the abrasion sensors 21 for a cutting ridge 26 to be used in FIG. 6 are brought into press contact with the distal ends of the probes 41. Thus, the conductive film circuit 21 is connected to the resistance meter via the probes 41.

During the cutting process, the throw-away tip 2 is abraded and, when a portion of the abrasion sensor 21 extending along the currently used cutting ridge 26 is abraded to its width, the abrasion sensor 21 is cut off, so that the electrical resistance becomes infinite. The portion of the abrasion sensor 21 extending along the cutting ridge 26 has a width which conforms to an allowable abrasion limit width. Therefore, when the abrasion sensor is abraded to the allowable abrasion limit width or chipped, the electrical resistance of the abrasion sensor 21 becomes infinite. The resistance meter is connected to a machining tool (not shown) designed to be able to stop the cutting process at this time point, whereby the cutting ridge 26 is prevented from being used over a use limit thereof and from being used in a chipped state.

Since neither the contacts between the abrasion sensor 21 and the probes 41 nor the lead wires are exposed to the outside, slug ejection is not hindered.

As described above, the ends 22 of the abrasion sensor 21 are kept in press contact with the probes 41. This is because loose contact between the abrasion sensor 21 and the probes 41 may result in momentary disconnection therebetween due to vibration occurring during the cutting process, and erroneous detection due to the momentary disconnection should be prevented.

Although the L-shaped lever 10 is employed for fixing the throw-away tip 2 to the holder in the aforesaid embodiment, a damper or a clamp bolt may be employed instead of the L-shaped lever 10.

Figure 7:
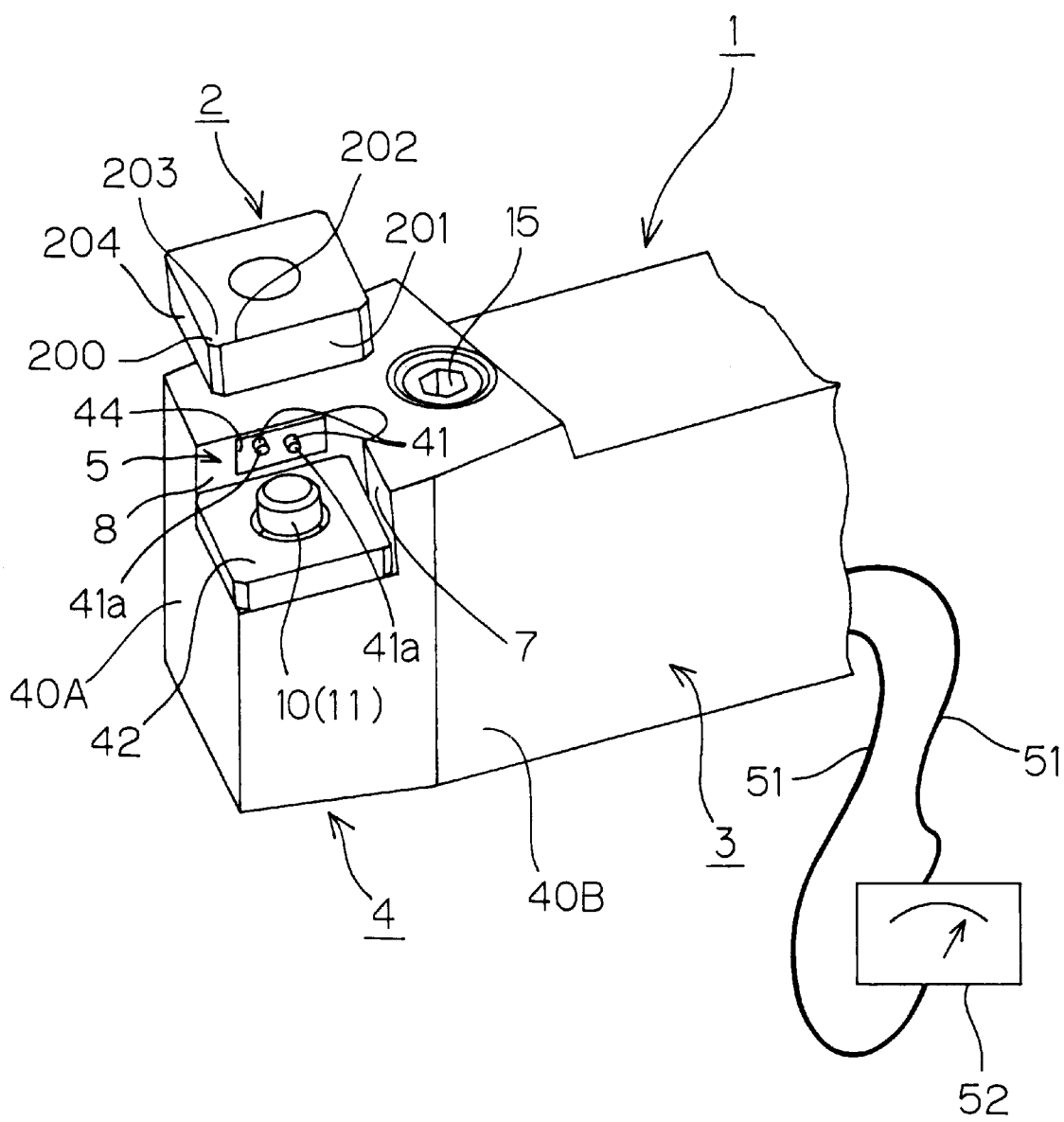
FIG. 7 is a diagram illustrating a holder for a throw-away tip in accordance with another embodiment of the invention.
Figure 8:
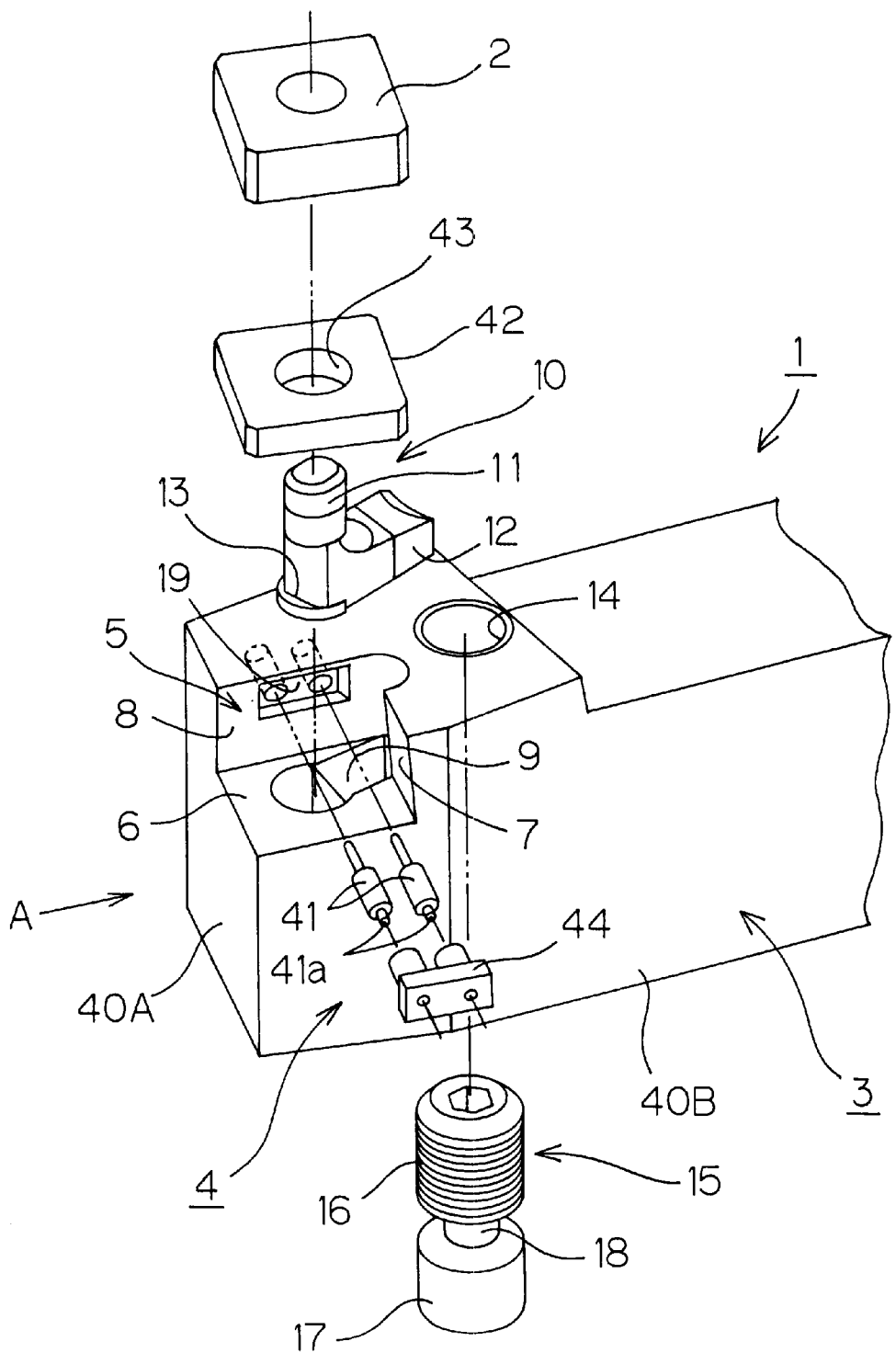
FIG. 8 is an exploded perspective view of the holder shown in FIG. 7.

FIG. 7 illustrates a holder 100 for a throw-away tip in accordance with another embodiment of the invention. FIG. 8 is an exploded perspective view of the holder 100 shown in FIG. 7. In FIGS. 7 and 8, the components of the holder 100 equivalent to those of the holder 1 are denoted by the same reference characters as in FIGS. 1 and 2, and no explanation will be given thereto.

In this embodiment, a probe insertion hole 19 is formed in the inward restriction surface 8 of the pocket 5. A pair of probes 41 are accommodated in the probe insertion hole 19. The pair of probes 41 are fixed to the tip mounting portion 4 in an electrically insulative manner by a single probe fixture 44.

Figure 9:
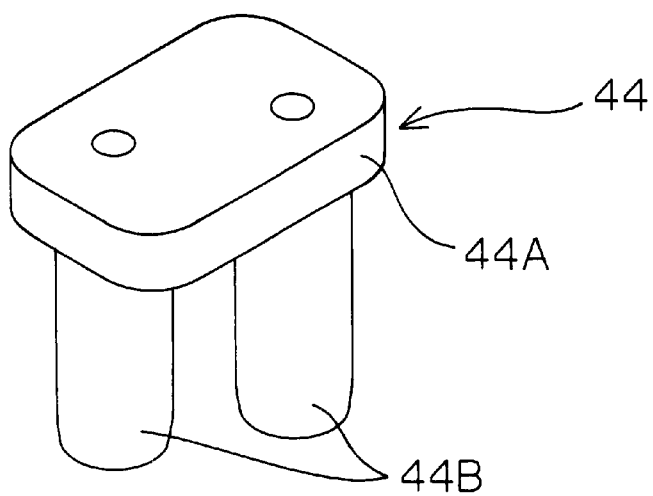
FIG. 9 is an enlarged perspective view of a probe fixture.
Figure 10:
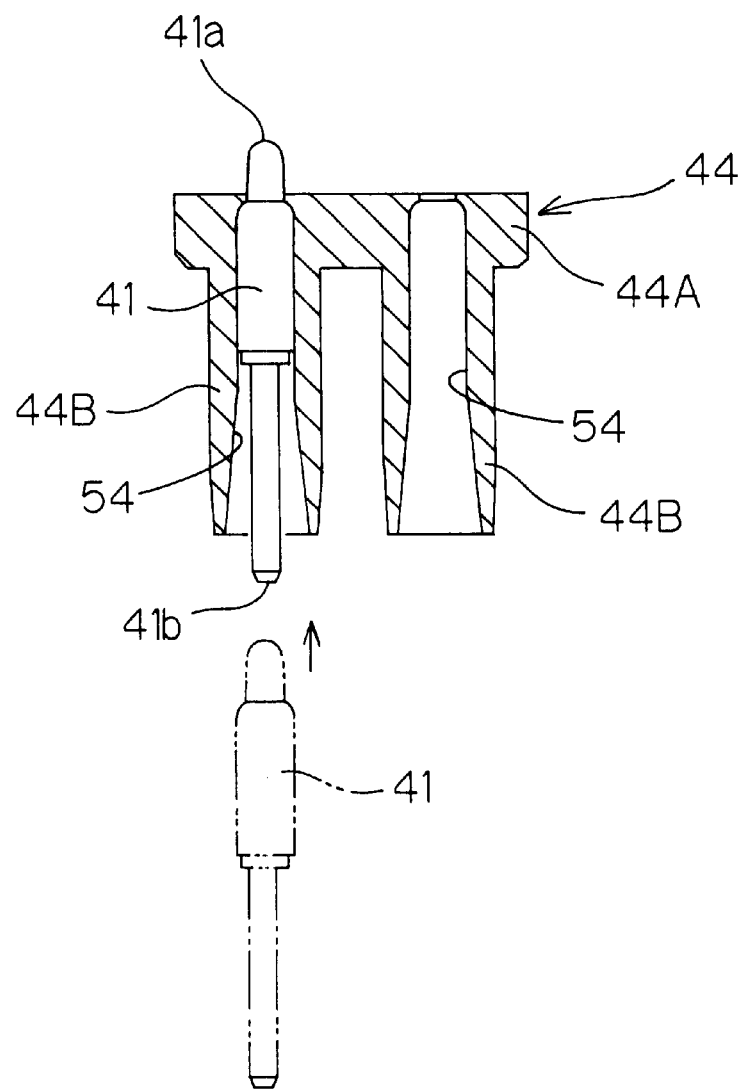
FIG. 10 is a diagram illustrating the probe fixture in vertical section and a probe engaged with the probe fixture.

FIG. 9 is an enlarged perspective view of the probe fixture 44 for fixing the probes 41, and FIG. 10 illustrates the probe fixture 44 in section and the probe 41 engaged with the probe fixture 44.

Referring to FIGS. 9 and 10, the probe fixture 44 is composed, for example, of a heat-resistant and electrically insulative resin. The probe fixture 44 has a base portion 44A of a generally rectangular plan shape, and projections 44B projecting from the base portion 44A. The probe fixture 44 is formed with two probe through-holes 54 for retaining the pair of probes 41 in a predetermined spaced relation. The probe through-holes 54 extend through the base portion 44A and the respective projections 44B. Lower portions of the probe through-holes 54 as seen in FIGS. 9 and 10 are flared for easy insertion of the probes 41. The probe through-holes 54 each have an inner diameter which is equal to the maximum outer diameter of the probes 41. The probes 41 are softly squeezed into the probe through-holes 54 from the lower side thereof as seen in FIG. 10 and fixed therein. After the insertion of the probes 41, distal ends 41a of the probes 41 project upward from the probe fixture 44 as seen in FIG. 10, and connection terminals 41b of the probes 41 project downward from the probe fixture 44 as seen in FIG. 10.

With the probes 41 fitted in the probe fixture 44, the probes 41 are electrically isolated from the tip mounting portion 4.

Figure 11:
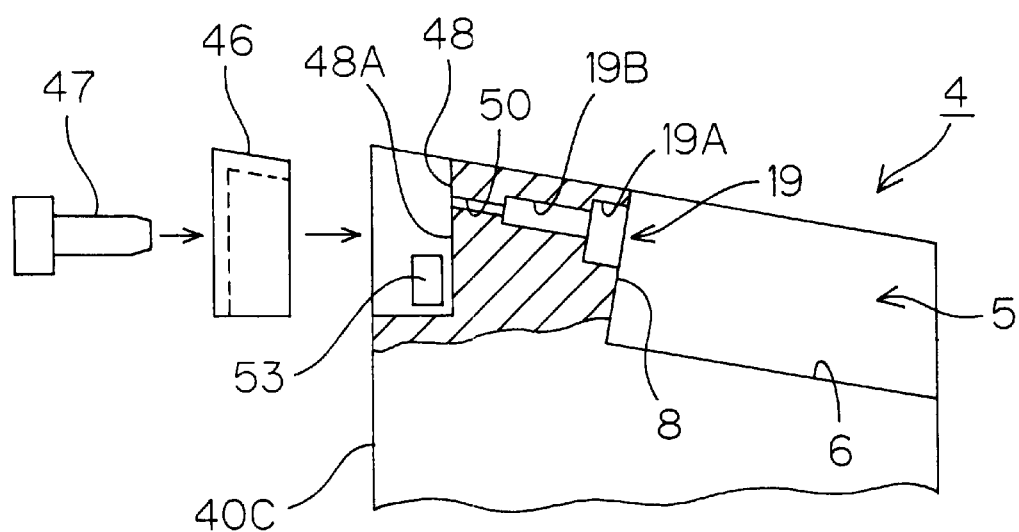
FIGS. 11 and 12 are diagrams of the holder as viewed in the direction of an arrow A in FIG. 8.
Figure 12:
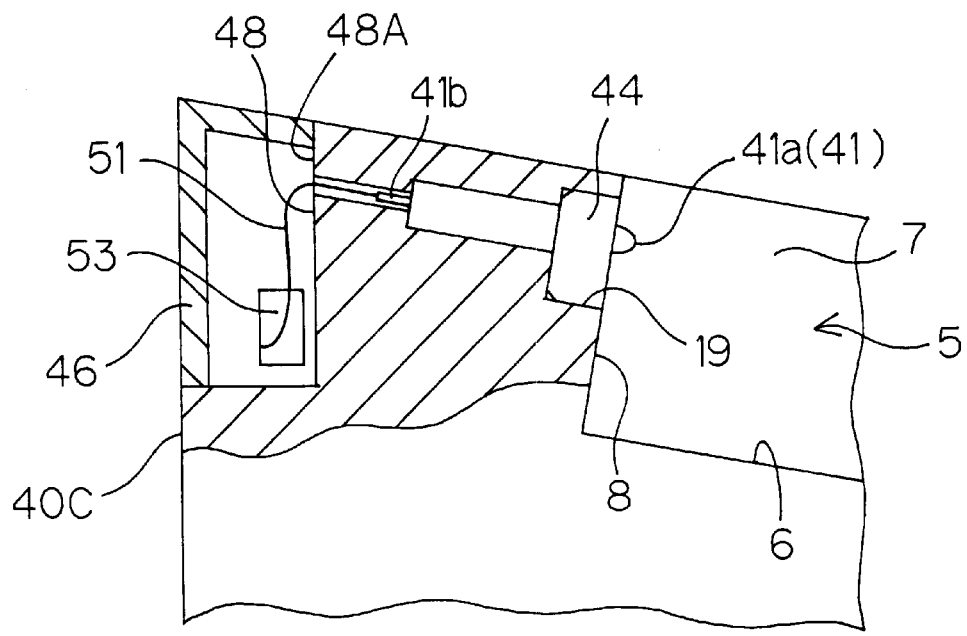

FIGS. 11 and 12 are diagrams of the holder 100 as viewed in the direction of an arrow A in FIG. 8. For convenience of explanation, an upper portion of the tip mounting portion 4 is partly removed in FIGS. 11 and 12.

Referring to FIG. 11, the probe insertion hole 19 has an engagement recess 19A opening into the inward restriction surface 8 and a pair of probe receiving holes 19B (only one of which is illustrated in FIG. 11) opening in an inward face of the engagement recess 19A. The engagement recess 19A receives the base portion 44A of the probe fixture 44, and the probe receiving holes 19B respectively receive the projections 44B of the probe fixture 44.

The tip mounting portion 4 is provided with a removable cover 46 which defines an upper portion of a side face 40C. The cover 46 is fixed to the tip mounting portion 4, for example, by a bolt 47. The side face 40C is formed with a recess 48 in which the cover 46 is fitted. Though not shown, a channel is formed in the inside of the holder 100, and two lead wires 51 are accommodated in the channel. A lead-out port 53 which communicates with the lead wire channel opens into a side face of the recess 48, for example. The recess 48 serves as a space for drawing out the lead wires 51.

Further, the tip mounting portion has through-holes 50 which extend from an inward face 48A of the recess 48 to inward ends of the probe receiving holes 19B of the probe insertion hole 19.

The probe fixture 44 is fitted in the probe insertion hole 19 as shown in FIG. 12, whereby the probes 41 can assuredly be fixed therein. With the probe fixture 44 thus fitted in the probe insertion hole, the connection terminals 41b of the probes 41 are respectively accommodated in the through-holes 50, and a forward face (an upper surface in FIG. 9) of the probe fixture 44 is substantially flush with the inward restriction surface 8. In this state, the distal ends 41a of the probes 41 slightly project laterally from the inward restriction surface 8, and are resiliently biased laterally by springs or the like incorporated in the probes 41. In this embodiment, one of the pair of probes 41 located on the left side in FIG. 7 is positioned at a slightly upper level than the other probe 41.

When the throw-away tip 2 is placed on the seat 42, the distal ends 41a of the probes 41 are brought into resilient contact with sensor contact portions provided on a side face of the throw-away tip 2. Thus, a resistance signal of the abrasion sensor of the throw-away tip 2 can be extracted to be applied to an external resistance meter 52 via the probes 41 and the lead wires 51 connected to the probes 41.

Since the tip mounting portion 4 has the removable cover 46 which defines the upper portion of the side face 40C thereof, an operation can easily be performed to electrically connect the lead wires drawn out of the lead-out port 53 to the connection terminals 41b of the probes 41.

With the cover 46 fixed to the tip mounting portion 4 with the bolt 47, the junctions between the probes 41 and the lead wires 51 are completely concealed, so that the cutting process can be performed without any trouble.

In the embodiment described above, a nose portion 200 located in a forward left corner of the throw-away tip 2 as seen in FIG. 7 and a cutting edge 202 located along an upper edge of a side flank 201 are mainly used for the cutting process. Therefore, stresses are generated in the cutting edge 202 directly serving for the cutting and in a portion of a rake face 203 of the throw-away tip 2 adjacent to the cutting edge 202 suffering from an attack by slugs during the cutting process, so that heat is generated to a high temperature. By the stresses generated in the throw-away tip 2, the cutting edge 202 and the rake face 203 are abraded and sometimes chipped. The chipping may cause breakage of the throw-way tip 2. That is, the chipping is liable to occur in the rake face 203 and the side flank 201 of the cutting portion of the tip 2 currently used for the cutting. Similarly, a stress is liable to be concentrated on a part of the tip mounting portion 4 of the holder 1 adjacent to the side face 40B located below the rake face 203 of the throw-away tip 2. Therefore, if the throw-away tip 2 is broken, the side face 40B is easily influenced by the breakage.

In this embodiment, the probe insertion hole 19 is provided in the inward restriction surface 8 of the tip mounting portion 4 which is less liable to be influenced by the chipping and the like of the throw-away tip 2.

Since the probe insertion hole 19 is thus provided in the inward restriction surface 8 of the tip mounting portion 4, there is a reduced possibility that the probes 41 within the probe insertion hole 19 are broken even if the throw-away tip 2 is broken.

Further, the provision of the probes 41 can be achieved by employing a simple structure. For the provision of the pair of probes 41 in juxtaposition in the inward restriction surface 8, it is merely necessary to form the probe insertion hole 19 in the single face, and the formation of the probe insertion hole 19 is relatively easy. In this case, an operation for connecting the lead wires 51 to the connection terminals 41b of the probes 41 can easily be performed.

Figure 13:
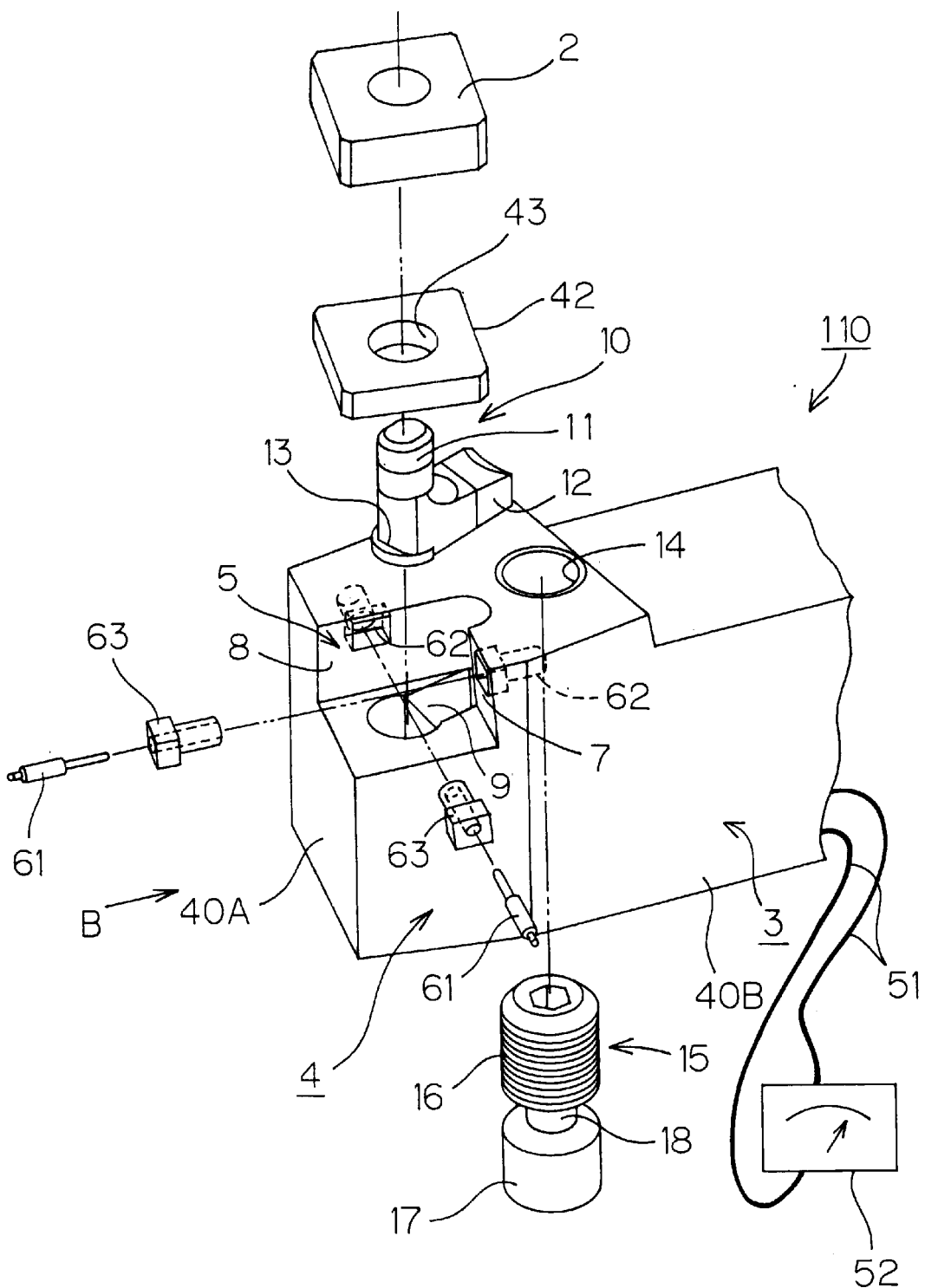
FIG. 13 is an exploded perspective view of a holder for a throw-away tip in accordance with further another embodiment of the invention.

FIG. 13 is an exploded perspective view of a holder 110 according to further another embodiment of the invention. In FIG. 13, components equivalent to those shown in FIGS. 1, 2, 7 and 8 are denoted by the same reference characters as in FIGS. 1, 2, 7 and 8, and no explanation will be given thereto. A difference between the holder 110 of this embodiment and the holder 100 of the embodiment shown in FIGS. 7 and 8 is that probes 61 are respectively provided on the rear restriction surface 7 and the inward restriction surface 8 of the pocket 5. More specifically, probe insertion holes 62 are respectively formed in the rear restriction surface 7 and the inward restriction surface 8, and the probes 61 are fixed therein by probe fixtures 63.

Figure 14:
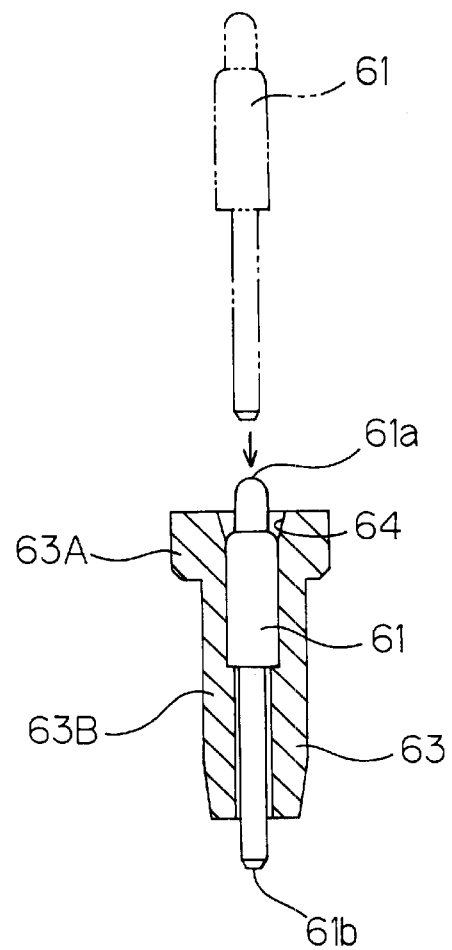
FIG. 14 is a diagram for explaining a probe fixture and a probe engaged with the probe fixture according to another embodiment of the invention.

FIG. 14 is a major sectional view for explaining the probe fixtures 63 and the probes 61 respectively engaged with the probe fixtures 63 according to this embodiment.

The probe fixtures 63 each have a base portion 63A of a generally square plan shape, and a projection 63B projecting from the base portion 63A. The probe fixture 63 has a probe through-hole 64 extending through the base portion 63A and the projection 63B. An upper portion of the probe through-hole 64 as seen in FIG. 14 is flared for easy insertion of the probe 61. The probe through-hole 64 has an inner diameter which is equal to the maximum outer diameter of the probe 61. The probe 61 is softly squeezed into the probe through-hole 64 from the upper side thereof as seen in FIG. 14 and fixed therein. After the insertion of the probe 61, a distal end 61a of the probe 61 projects upward from the probe fixture 63 as seen in FIG. 14, and a connection terminal 61b of the probe 61 projects downward from the probe fixture 63 as seen in FIG. 14.

Figure 15:
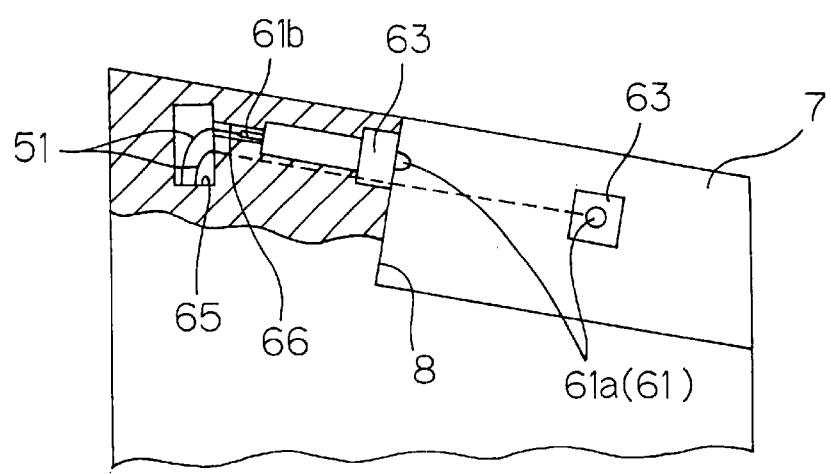
FIG. 15 is a diagram of the holder as viewed in the direction of an arrow B in FIG. 13.

Referring to FIG. 15, a lead wire channel 65 in which lead wires 51 are accommodated is provided inwardly of the inward restriction surface 8 in this embodiment. A channel 66 which communicates with the lead wire channel 65 extends from an inward end of the probe insertion hole 62.

The probe fixtures 63 are respectively fitted in the probe insertion holes 62, whereby the probes 61 can assuredly be fixed.

The connection terminal 61b of the probe 61 provided in the inward restriction surface 8 projects from the probe fixture 63, and is electrically connected to one of the lead wires 51 extending out of the lead wire channel 65. The other lead wire 51 connected to the probe 61 provided in the rear restriction surface 7 also extends out of the lead wire channel 65.

With the probe fixtures 63 fitted in the probe insertion holes, the distal end 61a of one of the pair of probes 61 slightly projects laterally from the inward restriction surface 8, and the distal end 61a of the other probe 61 slightly projects laterally from the rear restriction surface 7. The distal ends 61a of the probes 61 are respectively resiliently biased forward and leftward as seen in FIG. 13 by springs or the like incorporated in the probes 61.

When the throw-away tip 2 is placed on the seat 42, the distal ends 61a of the probes 61 are brought into resilient contact with sensor contact portions provided on side faces of the throw-away tip 2. Thus, a resistance signal of the abrasion sensor of the throw-away tip 2 can be extracted to be applied to an external resistance meter 52 via the probes 61 and the lead wires 51 connected to the probes 61.

During the cutting process, the rear restriction surface 7 and the inward restriction surface 8 are less liable to be influenced by breakage of the throw-away tip 2. Since the probe insertion holes 62 are thus provided in the rear restriction surface 7 and the inward restriction surface 8 of the tip mounting portion 4 in this embodiment, there is a reduced possibility that the probes 61 within the probe insertion holes 62 are broken even if the throw-away tip 2 is broken.

Figure 16A:
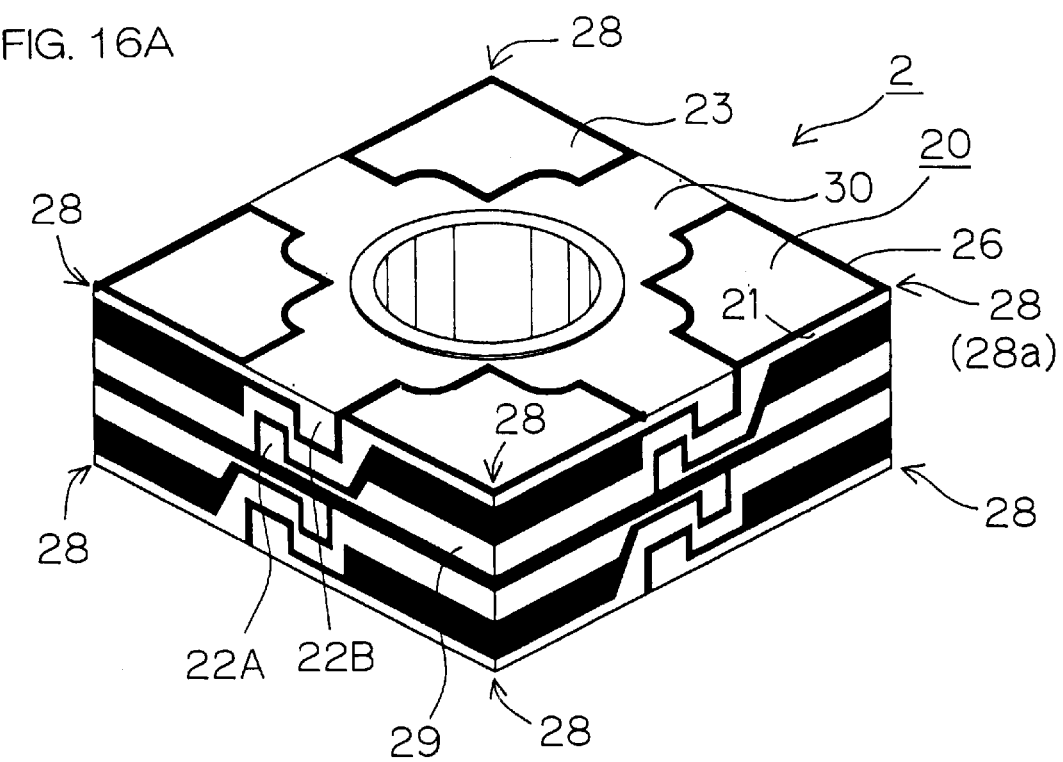
FIG. 16A is a perspective view illustrating the throw-away tip to be held by the holder according to the embodiment shown in FIG. 7 or 13 as viewed from the upper forward side.
Figure 16B:
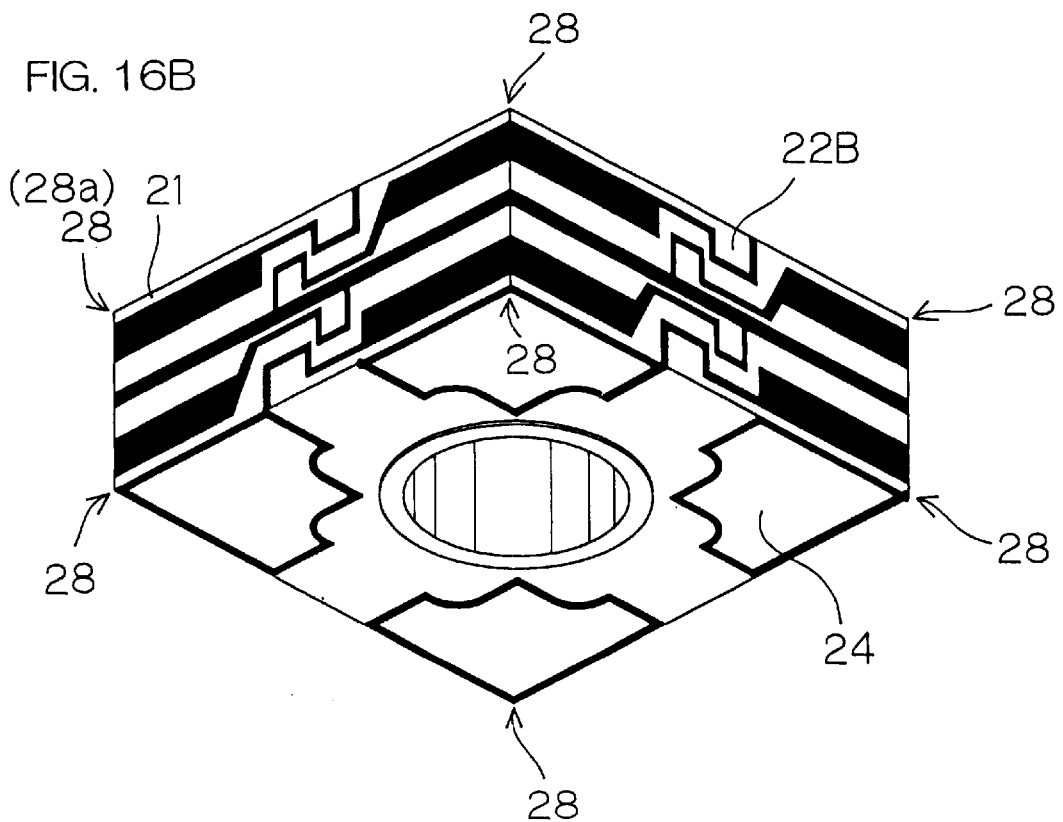
FIG. 16B is a perspective view illustrating the throw-away tip as viewed from the lower forward side.

FIGS. 16A and 16B illustrate the throw-away tip 2 to be attached to the holder 100 shown in FIG. 7 and the holder 110 shown in FIG. 13.

The throw-away tip 2 is of a so-called negative type in which cutting ridges on upper and lower sides thereof are usable for cutting. For convenience of explanation, one of opposite surfaces of the tip is called "upper face 23" and the other surface is called "lower face 24", though the tip 2 has no distinction between the upper and lower sides thereof.

The throw-away tip 2 has eight nose portions 28 on eight corners, as shown in FIGS. 16A and 16B, which are usable for the cutting. An explanation will be given to a case where an upper right nose portion 28a out of the eight nose portions 28 in FIG. 16A is used. An abrasion sensor 21 of a conductive film is provided as extending along a cutting ridge 26 on side faces defining the nose portion 28a. The abrasion sensor 21 extends to surround the nose portion 28 with its upper edge contacting the cutting ridge 26.

The side faces of the throw-away tip 2 are each divided into two portions, i.e., an upper side face portion and a lower side face portion, which are electrically insulated from each other. Pairs of sensor contact portions 22A, 22B are provided on the respective side face portions. When the nose portion 28a is used for cutting, a pair of sensor contact portions 22A, 22B disposed on an upper side face portion of a left side face in FIG. 16A are used for the electrical connection.

The abrasion sensor 21 is electrically connected to one 22A of the sensor contact portions via a connection line 29 extending on the side face as surrounding a nose portion 28 (an forward upper nose portion in FIG. 16A) adjacent to the nose portion 28a to be used. The abrasion sensor 21 is connected to the other sensor contact portion 22B via a connection region 30 provided on the upper face 23.

In the throw-away tip 2, sensor contact portions 22B in four pairs of sensor contact portions on the upper side face portions are electrically connected together, so that the one sensor contact portion 22A is electrically connected to all the sensor contact portions 22B on the upper side. Therefore, a sensor contact portion 22B on a right side face in FIG. 16B may be selected as a sensor contact portion to be paired with the one sensor contact portion 22A. That is, the throw-away tip 2 can be mounted on the holder 100 shown in FIG. 7 as well as on the holder 110 shown in FIG. 13.

When the throw-away tip 2 is mounted on the holder 100 (or 110), the sensor contact portions 22A and 22B of the abrasion sensor 21 for the nose portion 28a to be used as shown in FIG. 16A are respectively brought into press contact with the distal ends 41a (or 61a) of the probes 41 (or 61). Thus, the abrasion sensor 21 can be connected to the resistance meter via the probes 41 (or 61).

During the cutting process, the throw-away tip 2 is abraded and, when a portion of the abrasion sensor 21 extending along the currently used cutting ridge 26 is abraded to its width, the abrasion sensor 21 is cut off, so that the electrical resistance becomes infinite. The portion of the abrasion sensor 21 extending along the cutting ridge 26 has a width which conforms to an allowable abrasion limit width. Therefore, when the abrasion sensor is abraded to the allowable abrasion limit width or chipped, the electrical resistance of the abrasion sensor 21 becomes infinite. The resistance meter is connected to a machining tool (not shown) designed to be able to stop the cutting process at this time point, whereby the cutting ridge 26 is prevented from being used over the use limit thereof and from being used in a chipped state.

Since neither the contacts between the sensor contact portions 22A, 22B and the probes 41 (61) nor the lead wires are exposed to the outside, slug ejection is not hindered.

Although the L-shaped lever 10 is employed for fixing the throw-away tip 2 to the holder in the aforesaid embodiments, a clamper or a clamp bolt may be employed instead of the L-shaped lever 10.

Figure 17:
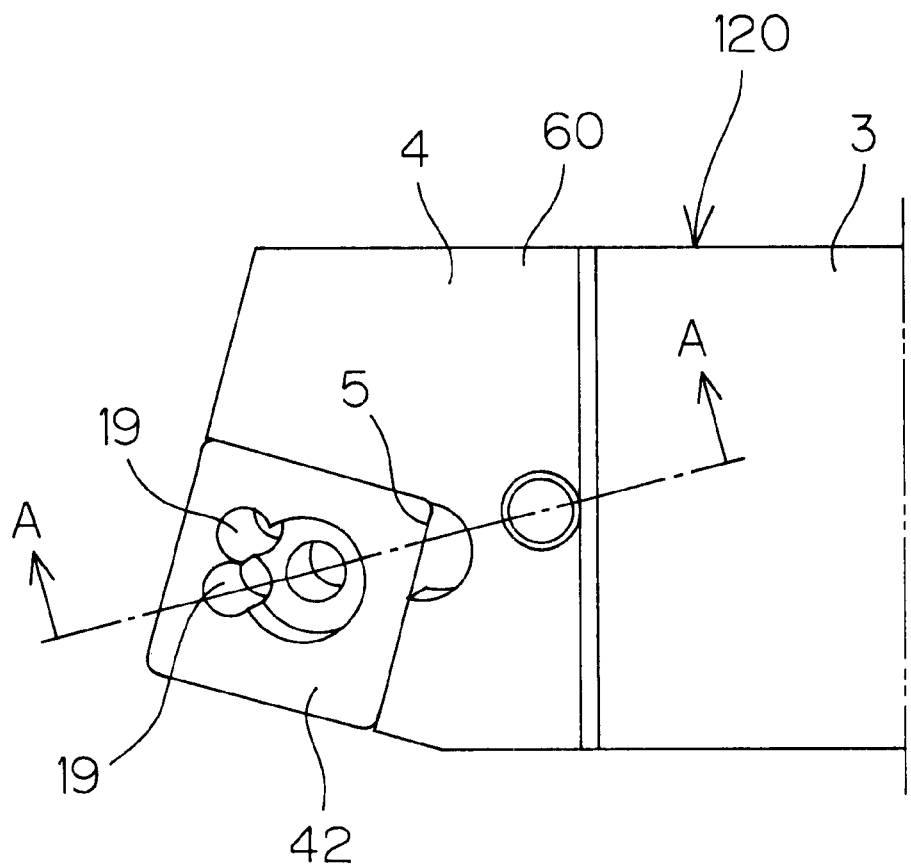
FIG. 17 is a diagram illustrating a holder according to still another embodiment of the invention.
Figure 18:
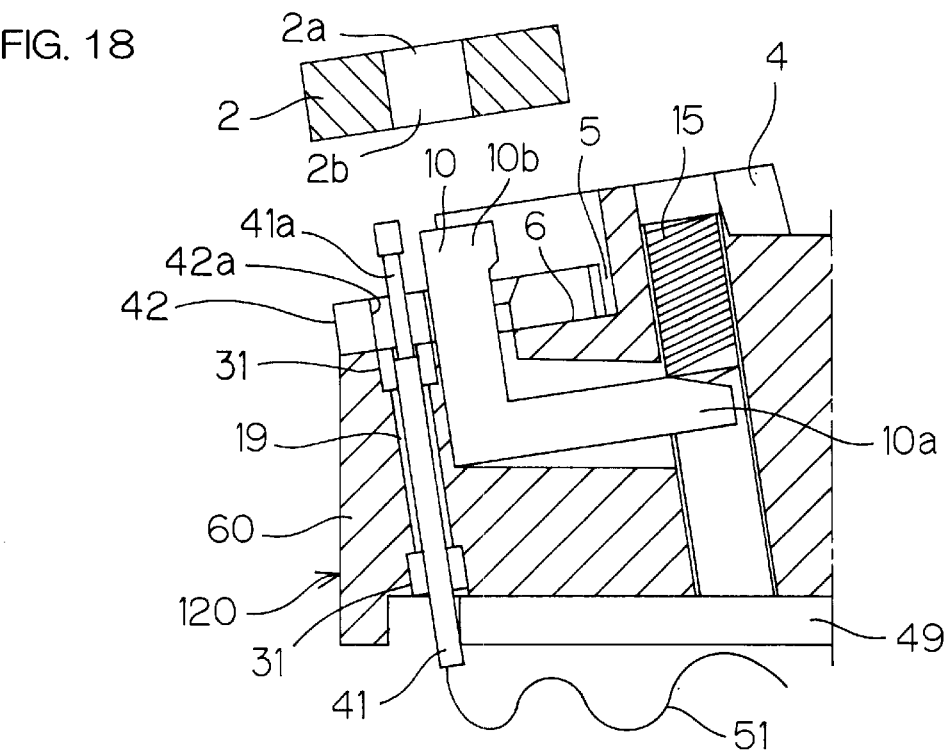
FIG. 18 is a sectional view taken along a line A—A in FIG. 17.
Figure 19:
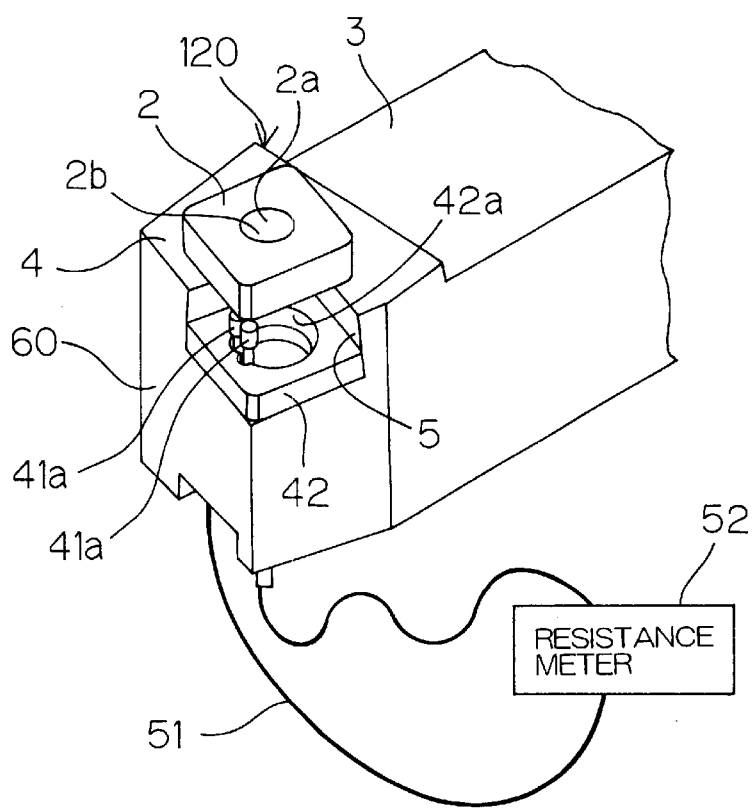
FIG. 19 is a perspective view of the holder shown in FIG. 17.

FIGS. 17, 18 and 19 illustrate a holder 120 according to still another embodiment of the invention. In FIGS. 17, 18 and 19, there are shown a throw-away tip 2, a pocket 5 for fixedly holding the throw-away tip 2, a tip mounting portion 4, a shank 3, probe insertion through-holes 19 opening toward the pocket 5, and probes 41.

The holder 120 has the tip mounting portion 4 provided at an end of the shank 3, and is adapted to fixedly hold the throw-away tip 2 in the pocket 5 provided in the tip mounting portion 4.

As shown in FIG. 18, the holder 120 is adapted to restrict the throw-away tip 2 with the use of an L-shaped lever 10. One end portion 10a of the L-shaped lever 10 is moved up and down by moving a clamp bolt 15 up and down. Thus, the L-shaped lever 10 is pivoted about a support point thereof, so that a interior wall 2b of a fixing hole 2a formed in the throw-away tip 2 is pressed or released by the other end portion 10b of the L-shaped lever 10. Thus, the throw-away tip 2 placed on the seat 42 is fixed to the holder 120.

The seat 42 serves as a protective member for preventing the holder 120 from being damaged by the throw-away tip 2 when the tip 2 is heavily damaged or chipped. A cemented carbide is mainly used as a material for the seat 42. If the seat 42 is composed of a softer material than the throw-away tip 2, the seat 42 is indented or deformed by a stress or vibration occurring during the cutting process, causing the throw-away tip 2 to wobble.

The tip mounting portion 4 of the holder 120 is formed with the pair of through-holes 19 which open toward the pocket 5 as shown in FIG. 17. The probes 41 to be brought into abutment against the throw-away tip 2 are respectively fitted in the through-holes 19 and fixed therein in an electrically insulative manner with respect to the holder 120.

For the electrical insulation of the probes, insulative sleeves 31 of an alumina-based ceramic or a heat-resistant resin are fitted around the probes 41, so that the probes 41 are fixedly supported by the insulative sleeves 31. The fixing of the probes 41 in the insulative sleeves 31 and the fixing of the insulative sleeves 31 in the holder 120 may be achieved by employing an adhesive or by thermal fitting.

In this embodiment, the probes 41 are composed of brass or stainless steel, and each include a contact rod 41 are silently supported by an elastic member (not shown) fitted in a bottom opening of a bottomed cylindrical member. The contact rods 41a of the probes project from a seat face 6 of the pocket 5 and extend through through-holes 42a formed in the seat 42 so as to be brought into press contact with the abrasion sensor 21 provided on the throw-away tip 2. Lower ends of the probes 41 are respectively connected to lead wires 51 by brazing or the like, and the lead wires 51 are connected to a resistance meter 52. Thus, the abrasion sensor 21 of the throw-away tip 2 is connected to the resistance meter 52 via the probes 41.

Further, the distal ends of the contact rods 41a of the probes 41 are each coated with a conductive rubber material not shown, whereby more intimate contact can be established between the contact rods 41a and the throw-away tip 2 for more stable detection of electrical signals.

The lead wires 51 connected to the lower ends of the probes 41 may be fixed in a groove 49 formed in an exterior surface of the holder 120 with a resin material not shown, so that the cutting process is not hindered by the lead wires 51. Alternatively, a hole for accommodating the lead wires 51 may be formed in a holder body 60 for this purpose.

What is claimed is:

1. A holder for a throw-away tip with a sensor, comprising:

a shank to be attached to a tool post; and a tip mounting portion provided at a distal end of the shank;

the tip mounting portion having a pocket for fixedly holding the throw-away tip;

the pocket opening into an upper face of the tip mounting portion, a front face of the tip mounting portion which is to be flush with a front flank of the throw-away tip, and a side face of the tip mounting portion which is to be flush with a side flank of the throw-away tip;

the pocket having a bottom face which serves as a seat face for receiving an under face of the throw-away tip placed thereon, and having a rear face and a side face which serve as restriction surfaces to be brought into abutment against side faces of the throw-away tip;

the tip mounting portion having a probe insertion hole which opens toward the pocket;

the tip mounting portion being provided with probes each having a distal end electrically connectable to the sensor of the throw-away tip and fitted in the probe insertion hole in an electrically insulative manner with respect to the tip mounting portion.

2. A holder as set forth in claim 1, wherein lead wires are respectively connected to proximal ends of the probes, and provided within a channel formed in the holder.

3. A holder for a throw-away tip with a sensor, comprising:

a shank to be attached to a tool post; and a tip mounting portion provided at a distal end of the shank;

the tip mounting portion having a pocket for fixedly holding the throw-away tip;

the pocket opening into an upper face of the tip mounting portion, a front face of the tip mounting portion which is to be flush with a front flank of the throw-away tip, and a side face of the tip mounting portion which is to be flush with a side flank of the throw-away tip;

the pocket having a bottom face which serves as a seat face for receiving an under face of the throw-away tip placed thereon, and having a rear face and a side face which serve as restriction surfaces to be brought into abutment against side faces of the throw-away tip;

the tip mounting portion having a probe insertion hole which opens toward the pocket;

the tip mounting portion being provided with probes each having a distal end electrically connectable to the sensor of the throw-away tip and fitted in the probe insertion hole in an electrically insulative manner with respect to the tip mounting portion, wherein lead wires are respectively connected to proximal ends of the probes, and provided within a channel formed in the holder, and wherein a seat is provided on the seat face of the pocket to be interposed between the seat face and the tip.

4. A holder as set forth in claim 3, wherein a probe fixture of an electrically insulative material is fitted in the probe insertion hole to fix the probes therein.

5. A holder as set forth in claim 4, wherein the distal ends of the probes are coated with a conductive rubber.

6. A holder as set forth in claim 4, wherein the tip mounting portion is provided with a removable cover, which is to be removed to expose the probes and the lead wires.

7. A holder for a throw-away tip with a sensor, comprising:

a shank to be attached to a tool post; and a tip mounting portion provided at a distal end of the shank;

the tip mounting portion having a pocket for fixedly holding the throw-away tip;

the pocket opening into an upper face of the tip mounting portion, a front face of the tip mounting portion which is to be flush with a front flank of the throw-away tip, and a side face of the tip mounting portion which is to be flush with a side flank of the throw-away tip;

the pocket having a bottom face which serves as a seat face for receiving an under face of the throw-away tip placed thereon, and having a rear face and a side face which serve as restriction surfaces to be brought into abutment against side faces of the throw-away tip;

the tip mounting portion having a pair of probe insertion holes which open into the seat face adjacent the front face thereof;

the tip mounting portion being provided with a pair of probes each having a distal end electrically connectable to the sensor of the throw-away tip and respectively fitted in the pair of probe insertion holes in an electrically insulative manner with respect to the tip mounting portion.

8. A holder for a throw-away tip with a sensor, comprising:

a shank to be attached to a tool post; and a tip mounting portion provided at a distal end of the shank;

the tip mounting portion having a pocket for fixedly holding the throw-away tip;

the pocket opening into an upper face of the tip mounting portion, a front face of the tip mounting portion which is to be flush with a front flank of the throw-away tip, and a side face of the tip mounting portion which is to be flush with a side flank of the throw-away tip;

the pocket having a bottom face which serves as a seat face for receiving an under face of the throw-away tip placed thereon, and having a rear face and a side face which serve as restriction surfaces to be brought into abutment against side faces of the throw-away tip;

the tip mounting portion having a probe insertion hole which opens into at least one of the restriction surfaces;

the tip mounting portion being provided with a pair of probes each having a distal end electrically connectable to the sensor of the throw-away tip and fitted in the probe insertion hole in an electrically insulative manner with respect to the tip mounting portion.

9. A holder as set forth in claim 8, wherein the probe insertion hole includes a pair of probe insertion holes, which are provided in juxtaposition in one of the two restriction surfaces.

* * * * *